US00PP15762P3

(12) United States Plant Patent
Zaiger et al.

(10) Patent No.: US PP15,762 P3
(45) Date of Patent: May 17, 2005

(54) INTERSPECIFIC TREE NAMED: FLAVOR WYNNE

(50) Latin Name: [*(Prunus salicina)×(Prunus salicina× Prunus armeniaca)*]
Varietal Denomination: Flavor Wynne

(76) Inventors: Gary Neil Zaiger, 1907 Elm Ave., Modesto, CA (US) 95358; Grant Gene Zaiger, 4005 California Ave., Modesto, CA (US) 95358; Leith Marie Gardner, 1207 Grimes Ave., Modesto, CA (US) 95358

( * ) Notice: Subject to any disclaimer, the term of this patent is extended or adjusted under 35 U.S.C. 154(b) by 462 days.

(21) Appl. No.: 10/315,259

(22) Filed: Dec. 10, 2002

(65) Prior Publication Data

US 2004/0111775 P1 Jun. 10, 2004

(51) Int. Cl.[7] ..... A01H 5/00

(52) U.S. Cl. ..... Plt./180
(58) Field of Search ..... Plt./180

*Primary Examiner*—Bruce R. Campell
*Assistant Examiner*—Anne Marie Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Regular bearer of medium to large fruit.
3. Fruit with good handling and shipping quality.
4. Fruit with very good flavor and eating quality.
5. Fruit with an attractive reddish maroon skin color.

1 Drawing Sheet

BACKGROUND OF THE VARIETY

FIELD OF THE INVENTION

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree [(*Prunus salicina*)×(*Prunus salicina*×*Prunus armeniaca*)] was originated and asexually reproduced by us in our experimental orchard located near Modesto, Stanislaus County, Calif.

PRIOR VARIETIES

The existing variety of plum trees (*Prunus salicina*) known to us and mentioned herein, are 'Red Beaut' Plum (U.S. Plant Pat. No. 2,539) and 'Santa Rosa' Plum (non-patented).

STATEMENT REGARDING FEDERALLY SPONSORED RESEARCH AND DEVELOPMENT

Not applicable.

ORIGIN OF THE VARIETY

The present new variety of interspecific tree [(*Prunus salicina*×(*Prunus salicina*×*Prunus armeniaca*)] was originated by us in our experimental orchard located near Modesto, Calif. as a first generation cross between proprietary lines of immediate parents with field identification numbers '57EC493' and '59EC558'. The maternal parent (57EC493) originated as a third generation seedling selection from open pollinated seed, which originated from 'Red Beaut' Plum (U.S. Plant Pat. No. 2,539). The pollen parent (59EC558), which is a plumcot, (*Prunus salicina*×*Prunus armeniaca*), originated as an open pollinated selected seedling of 'Red Beaut' Plum which crossed with an apricot (*Prunus armeniaca*) of unknown parentage. A large number of these first generation crosses were planted and grown on their own root system and, one such seedling, which is the present variety, exhibited desireable fruit characteristics and, in 1990, was selected for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct interspecific tree is of large size, vigorous, upright growth and a regular bearer of medium to large size fruit, with very good flavor and eating quality. The fruit is further characterized by having an attractive reddish maroon skin color, firm flesh with good handling and shipping quality and being relatively uniform in maturity and size throughout the tree. In comparison to 'Santa Rosa' Plum (non-patented), the maturity season is in the same time period, the fruit of the new variety is larger, more uniform in size, does not have pre-harvest drop of fruit and is more uniform in maturity. The winter chilling requirement is approximately the same for both varieties.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large. Usually pruned to 3 to 3.5 meters in height and width for economical harvesting of fruit.

*Vigor.*—Vigorous, growth of 1.5 to 2 meters in height the first growing season. Varies with fertility of soil, climatic conditions and cultural practices.

*Form.*—Upright. Usually pruned to vase shape.

*Branching habit.*—Upright. Crotch angle approximately 25°. As tree becomes productive, crop load increases crotch angle.

*Productivity.*—Medium, thinning and spacing of fruit necessary.

*Bearer.*—Regular, 4 consecutive years of adequate fruit set.

*Fertility.*—Self sterile, pollenizer required.

*Density.*—Medium dense. Prune to vase shape to allow sunlight and air movement to center of tree to enhance fruit color and health of fruit spurs.

*Hardiness.*—Hardy in all fruit growing areas of California. Winter chilling requirement approximately 800 hours at or below 45° F.

Trunk:

*Size.*—Medium stocky. Average circumference 43.2 cm at 22.9 cm from ground on a 6 year old tree.

*Texture.*—Medium shaggy, gets rougher with age.

*Color.*—Varies from 10YR 6/2 to 5YR 4/2.

Branches:

*Size.*—Medium to large. Average circumference 20.6 cm at 0.7 meters above ground. Crotch angle approximately 25°.

*Surface texture.*—New growth smooth. Mature growth medium rough, roughness increases with age.

*Lenticels.*—Medium to large. Average length 2.9 mm. Average width 0.7 mm. Color varies from 5YR 4/4 to 5YR 5/6. Average number of 49 in a 25.8 square cm surface of branch.

*Color.*—New growth varies from 2.5GY 6/6 to 2.5YR 4/4. Mature growth 5YR 3/2 to 5YR 3/4, varies with age of growth.

Leaves:

*Size.*—Medium. Average length 85.8 mm. Average width 27.4 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slightly indented over midrib, and leaf veins, glabrous. Lower surface relatively smooth, small ridges created by midrib and pinnate venation, glabrous.

*Petiole.*—Average length 17.7 mm. Average width 1.1 mm. Color 2.5GY 5/6. Longitudinally grooved. Glabrous.

*Glands.*—Reniform. Small. Average length 0.7 mm. Average diameter 0.4 mm. Average number 1, varies from 1 to 2. Located on base of leaf blade and upper portion of petiole. Color varies from 2.5GY 6/4 to 5GY 6/4.

*Color.*—Upper surface varies from 5GY 4/6 to 5GY 3/6. Lower surface varies from 5GY 6/4 to 5GY 5/4. Midvein color varies from 2.5GY 7/4 to 5GY 7/4.

Flower buds:

*Size.*—Small. Average length 8.1 mm. Average diameter 4.6 mm.

*Hardiness.*—Hardy in all stone fruit areas of California.

*Form.*—Conical, becomes slightly elongated just before opening.

*Pedicel.*—Long in length, thin in width, glabrous. Average length 7.0 mm. Average width 0.7 mm. Color 2.5GY 8/8.

*Color.*—N 9.5/.

*Number of buds per spur.*—Varies from 5 to 27. Average 17, varies with age of spurs.

Flowers:

*Size.*—Medium. Average height 9.8 mm. Average diameter 15.6 mm.

*Petals.*—Number 5, alternately arranged to sepals. Obovate, narrows at point of attachment. Size — medium. Average length 7.5 mm. Average width 6.7 mm. Margin — entire to slightly sinuate. Color — N 9.5/.

*Sepals.*—Number 5, alternately arranged to petals. Shape — acute, with a slightly rounded apex. Pubescence — upper surface glabrous, lower surface glabrous. Average length 2.7 mm. Average width 2.2 mm. Color — upper surface 2.5GY 7/8. Lower surface 2.5GY 6/8.

*Stamens.*—Average number per flower 30. Average filament length 6.0 mm. Filament color N 9.5/. Color of anthers 2.5Y 8/10.

*Pollen.*—Self sterile, pollenizer required. Color — 2.5Y 8/10.

*Pistil.*—Normally 1, varies from 1 to 2. Average length 9.7 mm. Surface — glabrous. Height — pistil and stamens approximately same height. Color — 10Y 8.5/6.

*Fragrance.*—Slight to moderate aroma.

*Blooming period.*—Date of First Bloom Feb. 20, 2002. Date of Petal Fall Feb. 28, 2002. Varies slightly with climatic conditions.

*Color.*—N 9.5/.

*Number flowers per flower bud.*—Usually 2, varies from 1 to 3.

*Pedicel.*—Long in length and thin in width, glabrous. Average length 10.9 mm. Average width 0.7 mm. Color 2.5GY 8/10.

Fruit:

*Maturity when described.*—Firm ripe.

*Date of first picking.*—Jun. 16, 2002.

*Date of last picking.*—Jun. 21, 2002, varies slightly with climatic conditions.

*Size.*—Medium to large. Average diameter axially 54.0 mm. Average transversely in suture plane 57.2 mm. Average weight 125 grams, average weight varies slightly with fertility of the soil, amount of thinning and climatic conditions.

*Form.*—Globose, slightly enlarged at apex.

*Suture.*—Shallow, extends from base to apex.

*Ventral surface.*—Nearly smooth, some fruit slightly lipped.

*Apex.*—Varies from rounded to slight projection.

*Base.*—Nearly flat, slightly retuse.

*Cavity.*—Rounded to slightly elongated. Average depth 6.1 mm. Average diameter 9.8 mm.

Stem:

*Size.*—Small. Average length 12.2 mm. Average diameter 1.8 mm.

*Color.*—Varies from 10Y 6/10 to 10Y 5/8.

Flesh:

*Ripens.*—Evenly.

*Texture.*—Firm, meaty.

*Fibers.*—Few, small, tender.

*Firmness.*—Firm, slightly firmer than 'Santa Rosa' Plum (non-patented).

*Aroma.*—Slight.

*Amydgalin.*—Undetected.

*Eating quality.*—Very good.

*Flavor.*—Very good, good balance between sugar and acid.

*Juice.*—Moderate, enhances flavor.

*Brix.*—Average 15.7°, varies slightly with amount of fruit per tree and climatic conditions.

*Color.*—Varies from 5Y 8.5/6 to 5Y 8/6. Pit cavity varies from 2.5Y 7/6 to 2.5Y 7/8.

Skin:

*Thickness.*—Medium.

*Surface.*—Smooth.

*Bloom.*—Moderate, complete coverage.

*Tendency to crack.*—None.

*Color.*—Ground color varies from 2.5Y 8/8 to 2.5Y 7/8. Overspread with 2.5R 2/4 to 5R 3/8.

*Tenacity.*—Tenacious to flesh.

*Astringency.*—Undetected.

Stone:

*Type.*—Semi-freestone.

*Size.*—Average length 23.8 mm. Average width 17.7 mm. Average depth 9.5 mm.

*Form.*—Ovoid.

*Base.*—Nearly flat, very slightly concaved.

*Apex.*—Slightly pointed. Average length 0.5 mm.

*Surface.*—Slightly pitted throughout, several small, narrow ridges extend from base about ⅓ of distance toward apex. A small, narrow groove on each side of suture.

*Sides.*—Unequal, one side extending further from suture plane.

*Ridges.*—Very small, narrow, relatively smooth.

*Tendency to split.*—None.

*Color.*—Varies from 10YR 7/8 to 10YR 6/8.

Kernal:

*Form.*—Ovate.

*Taste.*—Bitter.

*Viability.*—Viable, embryo fully developed.

*Size.*—Average length 14.5 mm. Average width 9.4 mm. Average depth 5.2 mm.

*Skin color.*—Varies from 2.5Y 8.5/6 to 2.5Y 8/6 when dry.

Use: Dessert. Market — local and long distance.

Keeping quality: Very good, held firm in cold storage 3 weeks at 38° to 42° F. without shriveling, internal breakdown of flesh, wooliness or appreciable loss of eating quality.

Shipping quality: Very good, showed minimal skin scarring or flesh bruising during picking, packing or shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct interspecific tree, substantially as illustrated and described, characterized by its large size, vigorous, upright growth and being a regular and productive bearer of medium to large fruit with very good flavor and eating quality and, in comparison to 'Santa Rosa' Plum (non-patented), the fruit ripens in the same maturity season, is larger and more uniform in size, does not have a preharvest drop and is more uniform in maturity.

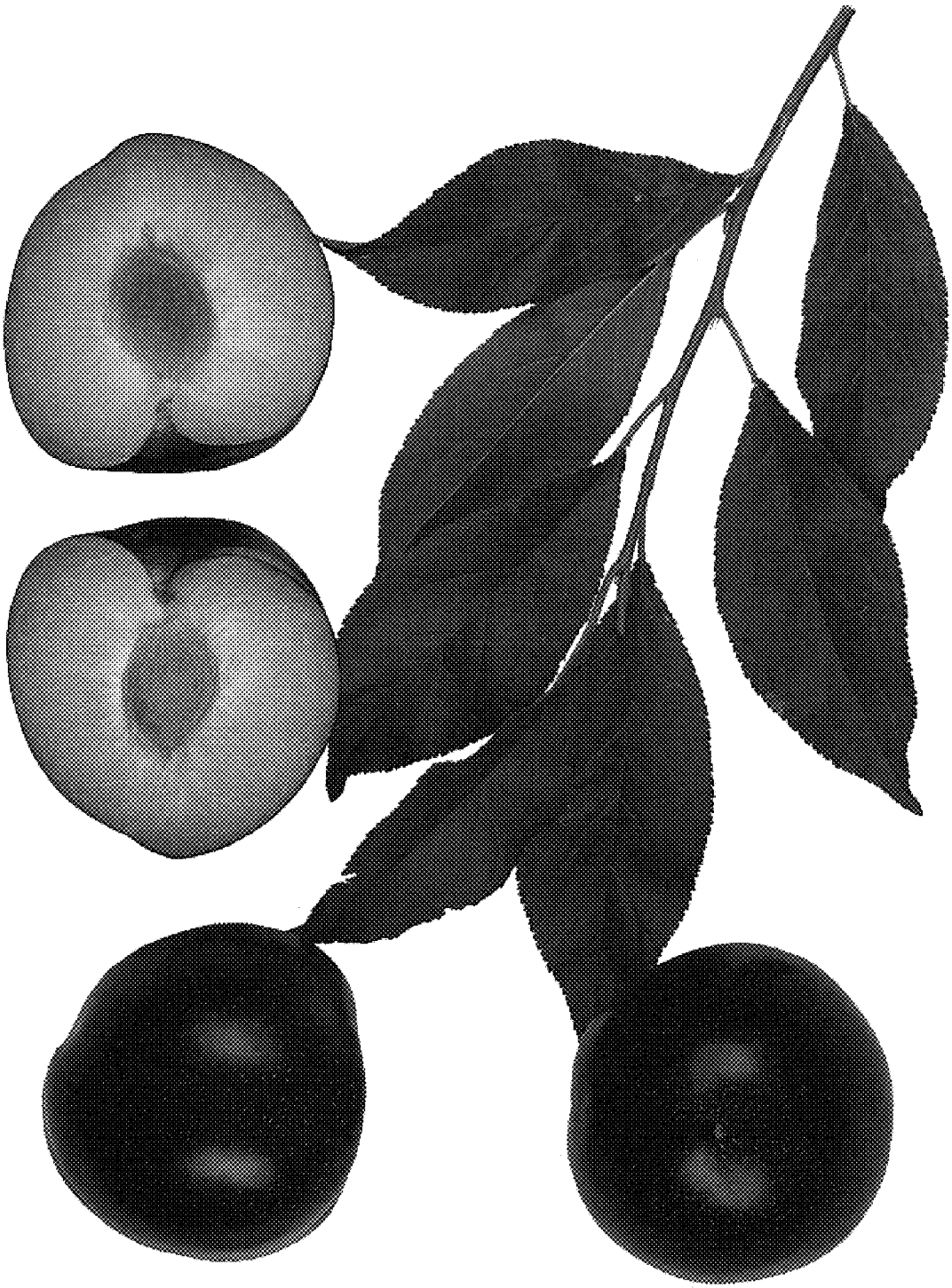

* * * * *